United States Patent [19]

Evetts

[11] Patent Number: 5,945,435
[45] Date of Patent: Aug. 31, 1999

[54] LEVOBUPIVACAINE AND ITS USE

[75] Inventor: Ian Ashley Evetts, Cambridge, United Kingdom

[73] Assignee: Darwin Discovery Limited, United Kingdom

[21] Appl. No.: 09/119,910

[22] Filed: Jul. 21, 1998

[30] Foreign Application Priority Data

Jul. 21, 1997 [GB] United Kingdom .................... 9715322
Oct. 17, 1997 [GB] United Kingdom .................... 9722023

[51] Int. Cl.⁶ ............................................. A61K 31/445
[52] U.S. Cl. ........................................................ 514/330
[58] Field of Search ............................................. 514/330

[56] References Cited

U.S. PATENT DOCUMENTS 4,695,576 9/1987 Ekenstam et al. .
5,708,011 1/1998 Bardsley et al. ......................... 514/330

FOREIGN PATENT DOCUMENTS 9500148 1/1995 WIPO .
9632109 10/1996 WIPO .

OTHER PUBLICATIONS

Rowland, Malcolm and Thomas N. Tozer (eds.) in: Clinical Pharmacokinetic Concepts and Applications, Chapter 7, pp. 83–88, (1995) Williams & Wilkins Publishers.

Mather, L.E. (1991) "Disposition of Mepivacaine and Bupivacaine Enantiomers in Sheep" British Journal of Anaesthesia 67:239–246.

Du Pen, Stuart L., et al. (1992) "Chronic epidural bupivacaine–opioid infusion in intractable cancer pain." Pain 49:293–300.

Honerjäger, P. (1986) "The Contribution of Na Channel Block to the Negative Inotropic Effect of Antiarrhythmic Drugs" Basic Res. Cardiol. 81(Suppl 1): 33–37.

Fozzard, Harry A. ad Andrew Wasserstrom (1985) "Voltage Dependence of Intracellular Sodium and Control of Contraction" in Zipes Dp, Jalife E. (eds.) Grune & Stratton, Orlando, pp. 51–57.

Schlepper, M. (1989) "Cardiodepressive effects of antiarrhythmic drugs" European Heart Journal 10(Suppl E):73–80.

Reiz, S. and S. Nath (1986) "Cardiotoxicity of Local Anaesthetic Agents" Er. J. Anaesth. 58:736–746.

De Jong, Rudolph H., Nancy L. David (1981) "Treating Bupivacaine Arrhythmias: Preliminary Report" Rg. Anesth. 6:99–103.

Strichartz, Gary R. (1988) "Neural Physiology and Local Anesthetic Action" In: Neural Blockade in Clinical Anesthesia and Management of Pain, Cousins MJ, Bridenbaugh PO (eds) JB Lippincott Company, Philadelphia, pp. 25–45.

Butterworth, J.F. et al. (1993) "Bupivacaine Inhibits Cyclic–3', 5'–Adenosine Monophosphate Production" Anesthesiology 79:88–95.

Mazoit, J.X. et al. (1993) "Myocardial Uptake of Bupivacaine: II. Pharmacokinetics and Pharmacodynamics of Bupivacaine Enantiomers in the Isolated Perfused Rabbit Heart" Anesth. Analg. 77(3):477–482.

Clarkson, C.W., L.M. Hondeghem (1985) "Mechanism for Bupivacaine Depression of Cardiac Conduction: Fast Block of Sodium Channels during the Action Potential with Slow Recovery from Block during Diastole" Anesthesiology 62:396–405.

Courtney, K.R., J.J. Kendig (1988) "Bupivacaine is an effective potassium channel blocker in heart" Biochimica et Biophysica Acta 939:163–166.

Denson, D.D. et al. (1992) "Enantiomer–Specific Effects of an Intravenously Administered Arrhythmogenic Dose of Bupivacaine on Neurons of the Nucleus Tractus Soliatrious and the Cardiovascular System in the Anesthetized Rat" Regional Anesthesia 17:311–316.

Vanhoutte, F. et al. (1991) "Stereoselective effects of the Enantiomers of Bupivacaine on the Electrophysiology Properties of the Guinea–Pig Papillary Muscle" Br. J. Pharmacol. 103:1275–1281.

Valenzuela, C. et al. (1994) "Stereoselective Bupivacaine Block of the Human Cardiac Delayed Rectifier Kv1.5 Channel" Biophys. J. 6:A205, abstract No. TU–Pos383.

Aps, C., F. Reynolds (1978) "An Intradermal Study of the Local Anaesthetic and Vascular Effects of the Isomers of Bupivacaine" Br. J. Clin. Pharmac. 6:63–68.

Burm, A.G.L. et al. (1994) "Pharmacokinetics of the Enantiomers of Bupivacaine Following Intravenous Administration of the Racemate" Br. J. Clin. Pharmac. 38:125–129.

Reynolds, F. (1995) "In Defence of Bupivacaine" International Journal of Obstetrics Anesthesia 4:93–108.

Testa, B. et al. (1990) "Racemates Versus Enantiomers in Drug Development: Dogmatism or Pragmatism?" Chirality, 2:129–133.

Rutten, A.J. et al. (1993) "Tissue Distribution of Bupivacaine Enantiomers in Sheep" Chirality 5(7):485–491.

Aberg, G. (1972) "Toxicological and Local Anesthetic Effects of Optically Active Isomers of Two Local Anaestnetic Compounds" Acta Pharmaceutica Et Toxicologica 31:273–286.

Kuhnert, B.R. et al. (1981) "Bupivacaine disposition in mother, fetus and neonate" Drug Disposition, p. 684; Abstract No. 2599.

Ariens, E.J. (1991) "Racemic Therapeutics–ethical and regulatory aspects" Eur. J. Clin. 41(2):89–93.

Rutten, A.J. et al. (1991) "Cardiovascular Effects and Regional Clearances of I.V. Bupivacaine in Sheep: Enantiomeric Analysis" Br. J. Anaesth. 67(3):247–256.

(List continued on next page.)

Primary Examiner—Raymond Henley, III
Attorney, Agent, or Firm—Saliwanchik, Lloyd & Saliwanchik

[57] ABSTRACT

Levobupivacaine is particularly suitable for use in anaesthetising a human patient prior to surgery that does not require hospitalisation for more than 12 hours after loss of motor block. Because of its beneficial motor block/sensory block characteristics, levobupivacaine can be used for 'daycare' surgery.

5 Claims, 2 Drawing Sheets

OTHER PUBLICATIONS

Luduena, F.P. et al. (1972) "Optical Isomers of Mepivacaine and Bupivacaine" *Arch. Int. Pharacodyn. Ther.* 200(2):359–369.

Rutten, A.J. et al. (1992) "Postoperative course of plasma protein binding of lignocaine, ropivacaine and bupivacaine in Sheep" *J. Pharm. Pharmacol.* 44(4):355–358.

Lee–Son, S. et al. (1992) "Stereoselective Inhibition of Neuronal Sodium Channels by Local Anaesthetics" Anesthesiology 77(2):324–355.

Wang, G.K., et al. (1992) "Altered Stereoselectivity of Cocaine and Bupivacaine Isomers in Normal and Batrachotoxin–modified Na+ Channels" J. Gen. Physiol. 100(6):1003–1020.

Luduena, F.P., et al. "Optical Isomers of an Aminoacyl Xylidide" Chemical Abstracts, vol. 73, No. 5, Aug. 3, 1970, Columbus, Ohio, U.S.; abstract No. 25314a.

Clark, B.J. et al. (1991) "Reversed–phase and Chiral High–Performance Liquid Chomatographic Assay of Bupivacaine and Its Enantiomers in Clinical Samples after Continuous Extrapleural Infusion" J. Chromatog. 553:383–390.

Ariens, E.J. (1990) "Racemische therapeutica probleemiddelen" Pharmaceutisch Weekblad 125:552–554.

Ariens, E.J. (1990) "Stereoselectivity in pharmacodynamics and pharmacokinetics" Schweiz. Med. Wochenschr. 120(5):131–134.

LEVOBUPIVACAINE AND ITS USE

FIELD OF THE INVENTION

This invention relates to a new therapeutic use for levobupivacaine or (S)-1-butyl-N-(2,6-dimethylphenyl)-2-piperidinecarboxamide.

BACKGROUND OF THE INVENTION

Racemic bupivacaine is an effective long-acting local anaesthetic, and may be given as an epidural. However, racemic bupivacaine is cardiotoxic, having depressant electrophysiological and mechanical effects on the heart. It should therefore be used with caution in cardiac-compromised patients, and the use of high doses and high concentrations is contraindicated.

In particular, bupivacaine has produced death in a number of patients, including women in childbirth and when used in the Bier's block technique. Although the incidence of death has been relatively small, the concern has been sufficient to stop the use of 0.75% bupivacaine for obstetrics and the proscribing of bupivacaine for use in Bier's blocks.

In addition, due to its mode of action, directly on the nervous system, at higher doses, bupivacaine is known to have undesirable central nervous system (CNS) side-effects which, prima facie, are connected to its anaesthetic activity. Indeed, the occurrence of CNS side-effects is one of the major factors limiting the use of this drug in normal clinical practice employing techniques such as local infiltration, nerve block, field block, epidural and spinal blocks.

It has been suggested that levobupivacaine is less cardiotoxic than dextrobupivacaine and racemic bupivacaine. See, for example, Vanhoutte et al, Br. J. Pharmacol. 103: 1275–1281 (1991), and Denson et al, Regional Anaesthesia 17:311–316 (1992). However, these reports are based on work in vitro, and cannot necessarily be extrapolated to any mammals, and certainly not to humans.

The effective utility of levobupivacaine in man, in vivo, is evidenced for the first time in WO-A-9510276, WO-A-9510277 and Gristwood et al, Exp. Opin. Invest. Drugs 3(11):1209–12 (1994). The latter documents indicate the potential utility of levobupivacaine in obstetrics, in part at least because of reduced CNS side-effects.

Gristwood et al also disclose that bupivacaine has "a beneficial ratio of sensory to motor blockade. This ratio is particularly important for obstetric use as it affords appropriate sensory block and yet allows women to consciously participate in the childbirth". Gristwood et al then report experiments comparing bupivacaine and levobupivacaine, and conclude that a "preliminary analysis of the data suggests that in terms of sensory block levobupivacaine has comparable efficacy to bupivacaine, with the duration of sensory block for 0.25% levobupivacaine being similar to that seen with bupivacaine 0.25%".

In many cases of surgery, there are both economic and practical reasons why hospital care should be relatively short. In the past, even for minor surgery, the patient might have been starved, given a full anaesthetic prior to surgery, and subsequently allowed to recover, involving hospital care for, say, 1 week. It is now realised that the same surgical procedure might be carried out with patient compliance, e.g. a coronary bypass may be conducted under local anaesthetic, with discharge after only 24 hours. This means that incisions are generally smaller, hospital beds can be made available more quickly, reduces patient stress and post-operative morbidity can be reduced, and the likelihood of good post-operative recovery is enhanced. Such "outpatient", "day-care" or "ambulatory" surgery requires the use of an anaesthetic that has a good ratio of sensory to motor blockade.

WO-A-9500148 discloses that ropivacaine salts provide sensory block and "minimal motor blockade". It is suggested that this effect is desirable, because reduced motor blockade (compared to bupivacaine) allows the patient to move, say, legs soon after operation.

SUMMARY OF THE INVENTION

While it has previously been shown that the use of levobupivacaine may have advantages over bupivacaine in certain areas, the available evidence suggests that there is no reason to prefer it in ambulatory surgery in general. This invention is based on the surprising discovery that the ratio of sensory to motor blockade (in terms of duration at least) is improved with respect to bupivacaine, thus making it an agent of choice for ambulatory surgery. In particular, while the depth of block is sufficient for surgery to be carried out safely, the duration of motor block is relatively short. This means that the patient is quickly able to move limbs, post-surgery. The patient's compliance and comfort are improved.

DESCRIPTION OF THE INVENTION

There are various embodiments of ambulatory surgery, in which levobupivacaine is suitably used, according to this invention (but which may exclude known uses, e.g. in pregnant women). They include orthopaedic surgery, vascular procedures on limbs, plastic surgery, burns treatment, maxillary facial surgery, abdominal or other general surgery, tonsillectomy, appendectomy, hysterectomy, hernia repair, ophthalmic surgery, and emergency surgery where there may be insufficient time for a full anaesthetic to be given and take effect. For example, in orthopaedic surgery, especially of the lower limb, the use of levobupivacaine provides early release of muscle block. An additional advantage is that undesirable shivering and cachexia may be reduced.

These procedures are characterised by the desire or need for patient compliance, and/or by the ability to treat and discharge the patient efficiently and quickly. In particular, they are characterised by the expectation that hospitalisation will not be required for more than 4, 6, 8, 10 or 12 hours after loss of motor block. Accordingly, the operation may be conducted, and the patient discharged, within a day.

In the method of the present invention, levobupivacaine may be provided as a bolus or in solution, for infusion or injection into the epidural or spinal space, or for administration by any of the conventional means for obtaining a nerve or field block. In addition to the anaesthetic blocks conventionally provided by the racemate, levobupivacaine may also be useful in providing blocks in areas of the body where the risk of systemic exposure to the drug, and therefore CNS side-effects, is particularly high. Examples include open wounds and vascular areas, for instance using intercostal blocks for the latter.

For upper limb surgery at least, infusion into the body near the base of the limb may be appropriate. A regional or plexus block may also be used.

Administration of levobupivacaine may be continuous or bolus administration. This may be done using conventional apparatus, e.g. including means for the patient to induce infusion as desired. An ambulatory pump may be used, as may ambulatory epidural administration.

The daily dose administered to the patient may be in the relatively low range known for the administration of racernic bupivacaine but, because of the decreased CNS side-effects of levobupivacaine, may be higher than the conventional dose for the racemic drug. For instance, the patient may receive a daily dose of levobupivacaine of up to 100, 150 or 200 mg.

The concentration of levobupivacaine to be given can be that conventionally used for the racemic drug. It may also be higher than this, for instance, at least 0.75% w/v, and can be up to 2% w/v. However, it appears that the effect that is sought in accordance with this invention, i.e. a high ratio of duration of sensory block: motor block can be seen especially at low concentrations, i.e. for surgery of the type to which this invention is particularly applicable. Thus, it may be preferred to use no more than 0.5% w/v, e.g. 0.25% w/v, levobupivacaine. This concentration may provide less motor block than a higher concentration, or the same concentration of racemate, when administered epidurally, e.g. for lower limb surgery. However, the higher concentration may increase sensory block.

The solution may typically be put up in unit doses of from 1 to 15 ml, and preferably of around 10 ml. However, the unit doses may be higher, for instance up to 40 ml or higher. The unit doses may be in the form of ampoules, which may be made of any suitable material, e.g. glass or an appropriately impervious plastic material. Unit dosages comprising at least 75 mg, but preferably less than 200 mg, of levobupivacaine can be administered, and more preferably the unit dosage is in the range 80 to 150 mg.

A preferred object of the invention is to achieve sensory block for 1 to 8 hours, and motor block for 25 or 50% less, e.g. 0.5 to 4 hours, dependent on the type of surgical procedures. This may be done following a single or continued administration.

The levobupivacaine used in the present invention is preferably substantially free of dextrobupivacaine, and is more preferably in at least 90%, and most preferably at least 99%, enantiomeric excess with respect to dextrobupivacaine. Throughout this specification, reference to bupivacaine and its enantiomers includes pharmaceutically-acceptable salts thereof.

If appropriate, levobupivacaine may be administered together with other agents such as fentanyl; see PCT/GB98/00658.

The following Study 1 provided the initial evidence, on which this invention is based.

Study 1

56 ASA I-III patients having major elective abdominal surgery were studied in a randomized, double-blind manner. Epidural anesthesia was initiated with 20 ml (3 ml 'Test' dose containing 15 µg epinephrine, followed by 17 ml plain solution) 0.75% levobupivacaine or 0.75% racernic bupivacaine over 5 minutes through an 18 gauge Tuohy needle at the L2-3 or L3-4 interspace. Sensory anesthesia to pinprick was tested at the end of injection, and 2, 5, 10, 15, 20, 25, 30 minutes and every 30 minutes thereafter, until complete resolution of blockade. Motor blockade of the lower extremities (modified Bromage scale) was assessed at 0, 10, 20 and 30 minutes, and every 30 minutes thereafter. Onset and adequacy of abdominal muscle relaxation were measured using the rectus abdominis muscle (RAM) test and by surgeon and anesthesiologist scoring.

Propofol±$N_2O$ were provided for sedation/light general anesthesia as desired. Muscle relaxants, opiates, and volatile anesthetics were excluded.

The planned surgical procedure was successfully completed in 53 patients with the initial 20 ml epidural injection; the remaining 3 patients (1 levobupivacaine and 2 bupivacaine) required a reinforcement dose (7 ml) of local anesthetic during surgery. Onset and regression of sensory blockade to the T10 dermatome, and total sensory duration, were equivalent between the groups (p=0.78 and p=0.22, respectively). Total sensory duration was longer with levobupivacaine (*p=0.022). Onset of motor blockade of the abdomen (RAM text≧3) was more rapid than in the lower extremities. Degree of motor block (Bromage scale≧2), was equal between groups, and was rated as 'good' or 'excellent' in 91% of patients. Duration of motor blockade was not significantly different between groups (p=0.31).

An important observation was that the duration of sensory block was significantly longer for levobupivacaine than bupivacaine. Secondly, although the degree of block was similar for both drugs, the trend was towards better block conditions during surgery and faster recovery (less motor block) after surgery, according to both surgeons and anaesthetists.

Since it is the ability of the patient to sit or ambulate early that is important post-surgery, it is relevant that levobupivacaine provided a faster offset of motor block. The patient could thus ambulate sooner, but had pain relief for longer.

Following the indication provided by Study 1, similar effects were observed at 0.5% of each drug. The following Study was then conducted by Professor M. Takasaki et al, of Miyazaki Medical College, Japan.

Study 2

This study was conducted on Sprague-Dawley rats weighing 250–390 g. The rats were individually housed in a temperature- and humidity-controlled environment with a 12-h light-dark cycle, with free access to food and water.

For epidural catherisation, the rats were anaesthetised by the intraperitoneal administration of pentobarbital sodium (50 mg/kg) (Nembutal sodium). The skin of the back was shaved, and 10% povidone iodine was applied. To flex the lower thoracic and lumber vertebrae, foam rubber was placed under the animal's abdomen during surgery. A skin incision was made on the midline of the spinous process of the T12 and L2 vertebrae. The fascia was opened, and superficial muscles were put aside. After the ligament was pierced between the T13 and L1 vertebrae, 20 mm ofthe length of aPE-10 catheter (ID 0.28 mm, OD 0.61 mm) was gently introduced into the epidural space. A drop of surgical glue (α-cyanoacrylate) was applied over the site of entry ofthe catheter. Another subcutaneous catheter site was provided, in the neck lesion. Benzylpenicillin potassium (0.3 U) and pentazocin (0.1 mg) were injected intramuscularly, and the skin lesion was closed.

Each animal was evaluated to ensure normal gait, motor and sensory responses, and rats were excluded from this experiment when they exhibited any neurological deficit, infection or another health problem after surgery (n=2). After surgery, rats were allowed to recover for 4 days before experimentation. Location of the distal end of the catheter was confirmed at the end of the experiment by injection of methylene blue, and dissection after anaesthesia following the intraperitoneal administration of pentobarbital sodium. Data obtained from animals in which the dye failed to stain the lumbar epidural space or in which the spinal cord was injured obviously were excluded from the data analysis (n=20).

The tail flick (TF) test was performed to measure the response to somatic stimulus. The time between stimulus onset and withdrawal of the tail from the heat source focused on the tail of approximately 5 cm from the tip was defined as the response latency. The device (Ugo Basile, Comerio-Varese, Italy) was given an average baseline latency of about 5 s. A cut-off latency was set up to 12 s, to prevent tissue damage. Mechanical nociception in the hind limbs was defined by the latency of the withdrawal response to application of the dental needle (30 G) to the hind paw. An average baseline latency was measured at about 0.3 s, and a cut-off latency was set at 2 s.

Motor blockade was defined as the animal's ability to walk on a smooth floor on which the animal would find difficulty in walking with full muscle power. Onset and duration of motor blockade were defined as the time from ending the injection of local anaesthetic to the time when the animal could no longer walk with its hind limbs. Duration of motor blockade was defined as the time from onset until the animal had regained the ability to walk with its hind limbs.

All animals were tested with only one of the dosages and one of the drugs. S(—)-bupivacaine HCI (levobupivacaine), racemic bupivacaine HCl and ropivacaine HCl were dissolved in distilled water (pH 5.1–5.5). After obtaining the baseline values, one of the drugs was administered at concentrations of 0.25% (2.5 mg/mL), 0.5% (5 mg/mL) and 0.75% (7.5 mg/mL). Drug administration was performed in a blinded, randomised fashion. Evaluation of sensory and motor blockade and statistical analysis of the data were also performed in a blinded manner. All drugs were injected at a volume of 100 $\mu$L administered manually over 2 min, followed by a 20 $\mu$L flush of normal saline. After epidural injection, TF latency and withdrawal latency of skin pinning to the hind limb were assessed every 5 min until the animal failed to respond on two consecutive occasions.

To assess the effect of epidural injections on sensory function, the data were converted to the maximum possible effect (MPE): % MPE=post-drug value—baseline value)/ (cut-off value—baseline value)×100%. Area under the time-effect curve (AUC) was calculated by accumulating the % MPE measured at fixed time intervals using the trapezoidal integration method. % MPE and AUC are presented as mean±SEM. Changes in % MPE and the differences in both AUC and the motor duration were compared using one-way analysis of variance, followed by Scheffe's post hoc test. Within each group, the results of repeated measures were analysed by repeated measures analysis of variance, followed by a paired t test. A difference of $P<0.05$ was considered statistically significant.

Figure 1:
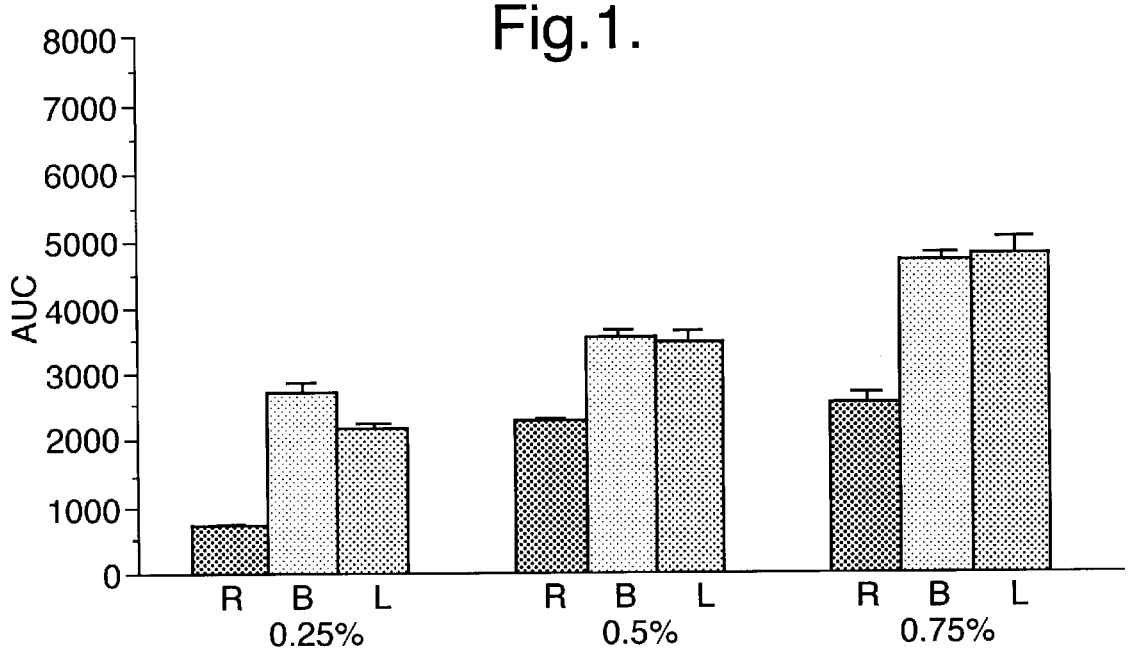
FIG. 1 is a chart of the AUC (area under curve) in the tail flick test after epidural administration of bupivacaine (B), levobupivacaine (L) and ropivacaine (R), each at 0.25%, 0.5% and 0.75%; n=6–10 for each group.
Figure 2:
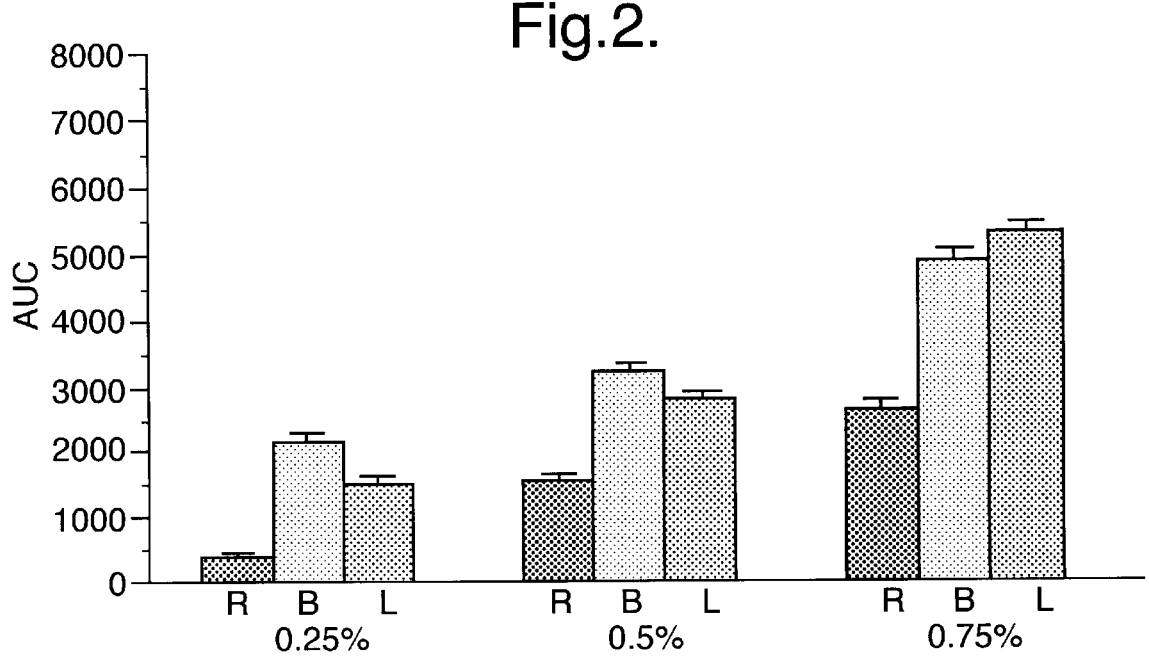
FIG. 2 is a chart of the AUC in the mechanical nociception in the hind limb for bupivacaine, levobupivacaine and ropivacaine, each at 0.25%, 0.5% and 0.75%; n=6–10 for each group. AUCs are calculated from time-effect curves of each rat for 60 min (0.25% and 0.5% group) or for 75 min (0.75%) after injection of drugs.
Figure 3:
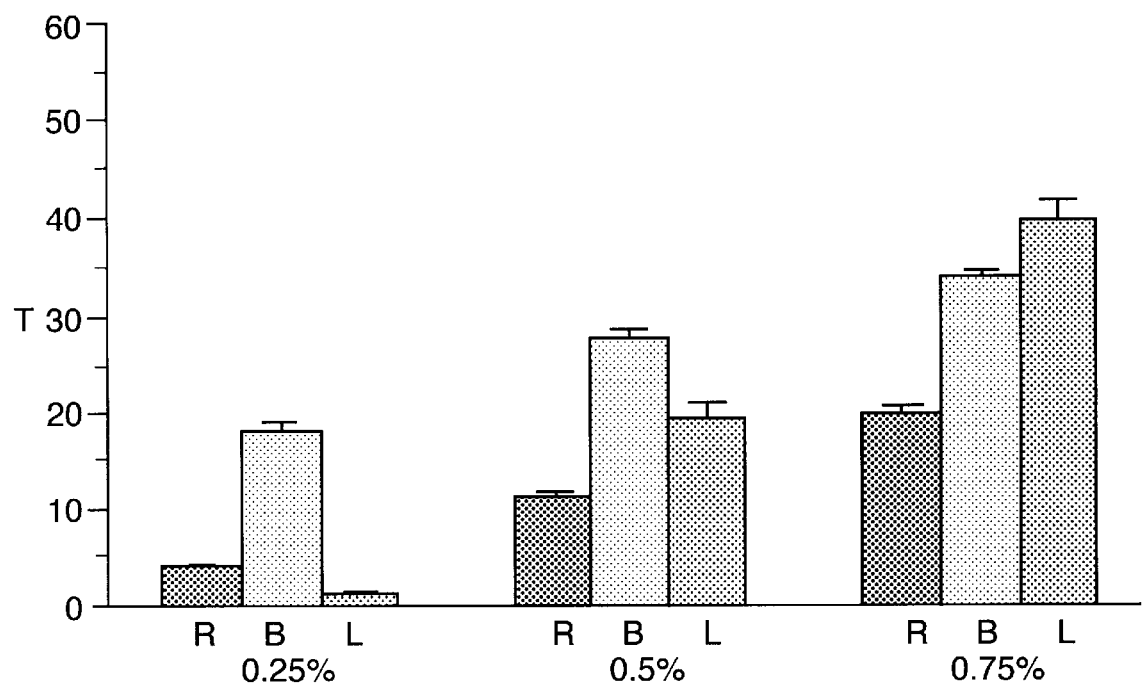
FIG. 3 is a chart showing the time (T; min) of the duration of motor block, after epidural injection of bupivacaine, levobupivacaine and ropivacaine, each at 0.25%, 0.5% and 0.75%; n=6–10 for each group.

These results show that the duration of motor block is surprisingly low, especially for low concentrations of levobupivacaine.

I claim:

1. A method of anaesthetising a human patient for surgery, wherein said method comprises the administration to said patient of an effective anaesthetic amount of levobupivacaine thereby producing sensory and motor block, wherein said levobupivacaine is presenting at least a 90% enantiomeric excess with respect to dextrobupivacaine, and wherein loss of said motor block occurs within 12 hours of its initiation.

2. The method, according to claim 1, wherein said surgery is selected from orthopaedic surgery, vascular procedures on limbs, plastic surgery, burns treatment, maxillary facial surgery, abdominal or other general surgery, tonsillectomy, appendectomy, hysterectomy, hernia repair, ophthalmic surgery, and emergency surgery.

3. The method, according to claim 1, wherein the hospitalisation after loss of motor block is no more than 8 hours.

4. The method, according to claim 1, wherein sensory and motor block are achieved for 10 minutes to 4 hours, and sensory block without motor block is achieved for all or at least a major part of the remaining period of hospitalisation.

5. The method, according to claim 1, wherein said anaesthetic is administered as solution containing no more than 0.5% levobupivacaine.

* * * * *

UNITED STATES PATENT AND TRADEMARK OFFICE
CERTIFICATE OF CORRECTION

PATENT NO.   :   5,945,435

DATED        :   August 31, 1999

INVENTOR(S)  :   Ian Ashley Evetts

It is certified that error appears in the above-identified patent and that said Letters Patent is hereby corrected as shown below:

Column 6, line 26: "levobupivacaineispresenting at leasta" should read --levobupivacaine is present in at least a--.

Signed and Sealed this

Twenty-fifth Day of January, 2000

Attest:

Attesting Officer

*Acting Commissioner of Patents and Trademarks*